(12) United States Patent
Kong et al.

(10) Patent No.: US 7,396,929 B2
(45) Date of Patent: Jul. 8, 2008

(54) SYNTHESIS OF 3-AMINO-4-SUBSTITUTED PYRAZOLE DERIVATIVES

(75) Inventors: Jianshe Kong, Franklin Park, NJ (US); Tao Meng, North Plainfield, NJ (US); Paul E. McNamara, Scotch Plains, NJ (US); Xian Liang, Monmouth Junction, NJ (US); Jesse K. Wong, Monroe Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 244 days.

(21) Appl. No.: 11/448,191

(22) Filed: Jun. 7, 2006

(65) Prior Publication Data

US 2006/0281756 A1      Dec. 14, 2006

Related U.S. Application Data

(60) Provisional application No. 60/688,995, filed on Jun. 9, 2005.

(51) Int. Cl.
*C07D 417/02* (2006.01)

(52) U.S. Cl. .................... 544/371; 546/211; 546/275.4; 548/190; 548/365.7

(58) Field of Classification Search ....................... None
See application file for complete search history.

(56) References Cited

U.S. PATENT DOCUMENTS 7,119,200 B2 * 10/2006 Guzi et al. .................. 544/281

* cited by examiner

*Primary Examiner*—Kamal A Saeed
(74) *Attorney, Agent, or Firm*—Patent Practitioners of Schering Corporation

(57) ABSTRACT

This application discloses a novel process to synthesize 3-amino-4-substituted pyrazole derivatives, which may be used, for example, as intermediates to prepare compounds having, for example, pharmaceutical utility.

25 Claims, No Drawings

SYNTHESIS OF 3-AMINO-4-SUBSTITUTED PYRAZOLE DERIVATIVES

CROSS REFERENCE TO RELATED APPLICATIONS

This application is based on and claims the priority of U.S. Provisional Application No. 60/688,995 filed on Jun. 9, 2005, which application is incorporated herein in its entirety by reference.

FIELD OF THE INVENTION

This application discloses a novel process to synthesize 3-amino-4-substituted pyrazole derivatives, which may be used, for example, as intermediates to prepare compounds having, for example, pharmaceutical utility.

BACKGROUND OF THE INVENTION

3-Amino-4-substituted pyrazole derivatives are used as intermediates in preparing organic compounds, such as pyrazololopyrimidine derivatives. Non-limiting examples of pyrazololpyrimidine derivatives that utilize 3-amino-4-substituted pyrazole derivatives include those having the general structure shown in Formula V:

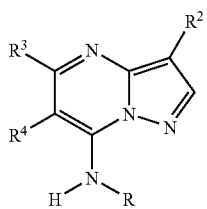

Formula V wherein:

R is H, alkyl, alkenyl, alkynyl, arylalkyl, arylalkenyl, cycloalkyl, cycloalkylalkyl, alkenylalkyl, alkynylalkyl, heterocyclyl, heterocyclylalkyl, heteroarylalkyl (including N-oxide of said heteroaryl), —(CHR$^5$)$_n$-aryl, —(CHR$^5$)$_n$-heteroaryl,

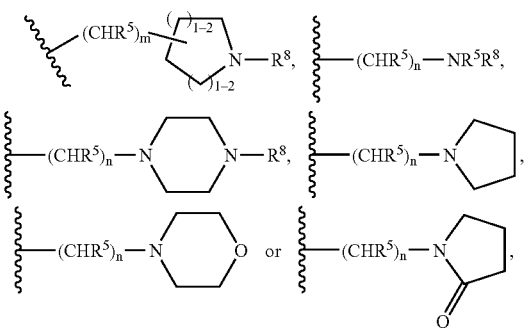

wherein each of said alkyl, alkenyl, alkynyl, aryl, cycloalkyl, heterocyclyl, and heteroaryl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^5$R$^{10}$, —C(R$^4$R$^5$)$_p$—R$^9$, —N(R$^5$)Boc, —(CR$^4$R$^5$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^2$ is selected from the group consisting of R$^9$, alkyl, alkenyl, alkynyl, CF$_3$, heterocyclyl, heterocyclylalkyl, halogen, haloalkyl, aryl, arylalkyl, heteroarylalkyl, alkynylalkyl, cycloalkyl, heteroaryl, alkyl substituted with 1-6 R$^9$ groups which can be the same or different and are independently selected from the list of R$^9$ shown below, aryl substituted with 1-3 aryl or heteroaryl groups which can be the same or different and are independently selected from phenyl, pyridyl, thiophenyl, furanyl and thiazolo groups, aryl fused with an aryl or heteroaryl group, heteroaryl substituted with 1-3 aryl or heteroaryl groups which can be the same or different and are independently selected from phenyl, pyridyl, thiophenyl, furanyl and thiazolo groups, heteroaryl fused with an aryl or heteroaryl group,

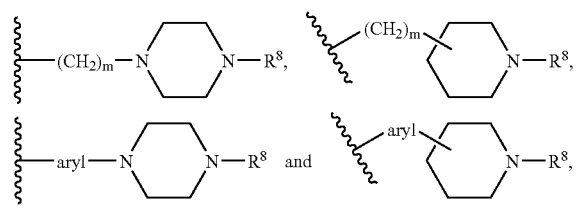

wherein one or more of the aryl and/or one or more of the heteroaryl in the above-noted definitions for R$^2$ can be unsubstituted or optionally substituted with one or more moieties which can be the same or different, each moiety being independently selected from the group consisting of halogen, —CN, —OR$^5$, —SR$^5$, —S(O$_2$)R$^6$, —S(O$_2$)NR$^5$R$^6$, —NR$^5$R$^6$, —C(O)NR$^5$R$^6$, CF$_3$, alkyl, aryl and OCF$_3$;

R$^3$ is selected from the group consisting of H, halogen, —NR$^5$R$^6$, —OR$^6$, —SR$^6$, —C(O)N(R$^5$R$^6$), alkyl, alkynyl, cycloalkyl, aryl, arylalkyl, heterocyclyl, heterocyclylalkyl, heteroaryl and heteroarylalkyl,

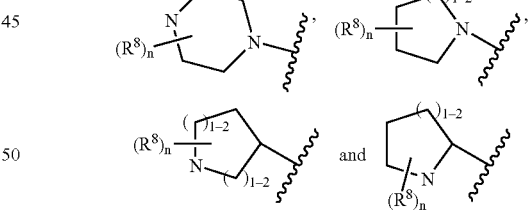

wherein each of said alkyl, cycloalkyl, aryl, arylalkyl, heterocyclyl, heterocyclylalkyl, heteroaryl and heteroarylalkyl for R$^3$ and the heterocyclyl moieties whose structures are shown immediately above for R$^3$ can be unsubstituted or optionally independently substituted with one or more moieties which can be the same or different, each moiety being independently selected from the group consisting of halogen, alkyl, aryl, cycloalkyl, CF$_3$, CN, —OCF$_3$, —(CR$^4$R$^5$)$_p$OR$^5$, —OR$^5$, —NR$^5$R$^6$, —(CR$^4$R$^5$)$_p$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$, with the proviso that no carbon adjacent to a nitrogen atom on a heterocyclyl ring carries a —OR$^5$ moiety;

$R^4$ is H, halo or alkyl;

$R^5$ is H, alkyl, aryl or cycloalkyl;

$R^6$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, $-OR^5$, $-NR^5R^{10}$, $-C(R^4R^5)_p-R^9$, $-N(R^5)Boc$, $-(CR^4R^5)_pOR^5$, $-C(O_2)R^5$, $-C(O)R^5$, $-C(O)NR^5R^{10}$, $-SO_3H$, $-SR^{10}$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, $-OR^5$, $-NR^4R^5$, $-C(R^4R^5)_p-R^9$, $-N(R^5)Boc$, $-(CR^4R^5)_pOR^5$, $-C(O_2)R^5$, $-C(O)NR^4R^5$, $-C(O)R^5$, $-SO_3H$, $-SR^5$, $-S(O_2)R^7$, $-S(O_2)NR^4R^5$, $-N(R^5)S(O_2)R^7$, $-N(R^5)C(O)R^7$ and $-N(R^5)C(O)NR^4R^5$; or optionally (i) $R^5$ and $R^{10}$ in the moiety $-NR^5R^{10}$, or (ii) $R^5$ and $R^6$ in the moiety $-NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, arylalkenyl, heteroaryl, arylalkyl, heteroarylalkyl, heteroarylalkenyl, and heterocyclyl, wherein each of said alkyl, cycloalkyl, heterocyclylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-CH_2OR^5$, $-C(O_2)R^5$, $-C(O)NR^5R^{10}$, $-C(O)R^5$, $-SR^{10}$, $-S(O_2)R^{10}$, $-S(O_2)NR^5R^{10}$, $-N(R^5)S(O_2)R^{10}$, $-N(R^5)C(O)R^{10}$ and $-N(R^5)C(O)NR^5R^{10}$;

$R^8$ is selected from the group consisting of $R^6$, $-OR^6$, $-C(O)NR^5R^{10}$, $-S(O_2)NR^5R^{10}$, $-C(O)R^7$, $-C(=N-CN)-NH_2$, $-C(=NH)-NHR^5$, heterocyclyl, and $-S(O_2)R^7$;

$R^9$ is selected from the group consisting of halogen, $-CN$, $-NR^5R^{10}$, $-C(O_2)R^6$, $-C(O)NR^5R^{10}$, $-OR^6$, $-SR^6$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

m is 0 to 4;

n is 1 to 4; and p is 1 to 4, with the proviso that when $R^2$ is phenyl, $R^3$ is not alkyl, alkynyl or halogen, and that when $R^2$ is aryl, R is not

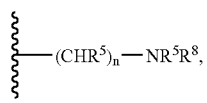

and with the further proviso that when R is arylalkyl, then any heteroaryl substituent on the aryl of said arylalkyl contains at least three heteroatoms, as well as, any solvates, polymorphs, position isomers and stereo isomers of these compounds. These compounds are disclosed in U.S. Pub. No. US 2004/0209878 A1, published on Oct. 21, 2004 and herein incorporated by reference. The compounds of Formula V can be useful as protein kinase inhibitors and can be useful in the treatment and prevention of proliferative diseases, for example, cancer, inflammation and arthritis. These compounds may also be useful in the treatment of neurodegenerative diseases such Alzheimer's disease, cardiovascular diseases, viral diseases and fungal diseases.

US Pub. No. 2004/0209878 A1 discloses a process to prepare 3-amino-4-substituted pyrazole derivatives of the formula

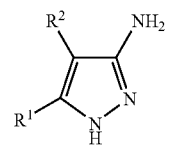

through the general route described below in Scheme 1. Treatment of the

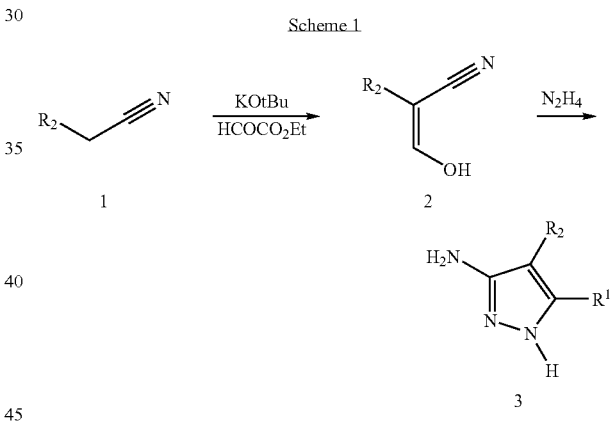

starting nitrile 1 with potassium t-butoxide and ethyl formate gives rise to the intermediate enol 2 which upon treatment with hydrazine gives the desired substituted 3-aminopyrazole 3.

Okazaki et al. (*Chem. Pharm. Bull.*, 46(1) 69-78 (1998) describe a method for synthesizing 3-amino-5-ethyl-1H-pyrazole that comprises adding acetonitrile to a suspension containing sodium amide and liquid ammonia with stirring followed by the addition of methyl propionate. After removing the ammonia, the mixture is subsequently mixed with ethanol and hydrazine hydrate. Okazaki et al. report that the 3-amino-4-ethyl-1H-pyrazole is also made by following this procedure.

Springer et al. (*J. Med. Chem.*, 25 235-242 (1982) disclose an alternative process to prepare 3-amino-4-ethylpyrazole that involves adding ethyl formate and n-butyronitrile to a suspension of sodium metal in anhydrous ether to form alpha-formyl-n-butyronitrile which, in a separate step, was treated with hydrazine hydrate in glacial acetic acid. Springer et al. report a yield of 21%.

Ullas et al. (*J. Org. Chem.*, 53(11) 2413-2418 (1988) and Smirnow and Hopkins (*Synthetic Comm.* 16(10) 1187-1193 (1986) prepare a 3-amino pyrazole derivative or 5-alkylcytosine derivatives respectively using a cyclization reaction involving hydrazine. JP 10-29980 discloses a 4-step synthetic route to prepare 3-amino-4-alkyl-pyrazoles. In a process for preparing 9-(arylmethyl) derivatives, Montgomery et al. (*J. Med. Chem.*, 36(1) 55-69(1993)) describe a process for synthesizing 2-formyl-3-(het)aryl-propanenitriles from the corresponding 3-aryl- or 3-heteroaryl-propanenitrile by treating the 3-aryl- or 3-heteroaryl-propanenitrile with sodium hydride in THF followed by the addition of ethyl formate.

In view of the importance of pyrazololopyrimidine compounds, new methods for preparing intermediates used in the synthesis of these compounds is always of interest, especially where the novel method is more economical and produces the intermediate in a higher yield than the prior processes.

SUMMARY OF THE INVENTION

In an embodiment, the present application teaches a novel, simple process of making a 3-amino-4-substituted pyrazole derivative of the formula:

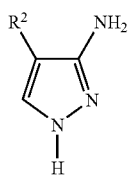

(I)

in which $R^2$ is selected from the group consisting of $R^9$, alkyl, alkenyl, alkynyl, $CF_3$, heterocyclyl, heterocyclylalkyl, halogen, haloalkyl, aryl, arylalkyl, heteroarylalkyl, alkynylalkyl, cycloalkyl, heteroaryl, alkyl substituted with 1-6 $R^9$ groups which can be the same or different and are independently selected from the list of $R^9$ shown below, aryl substituted with 1-3 aryl or heteroaryl groups which can be the same or different and are independently selected from phenyl, pyridyl, thiophenyl, furanyl and thiazolo groups, aryl fused with an aryl or heteroaryl group, heteroaryl substituted with 1-3 aryl or heteroaryl groups which can be the same or different and are independently selected from phenyl, pyridyl, thiophenyl, furanyl and thiazolo groups, heteroaryl fused with an aryl or heteroaryl group,

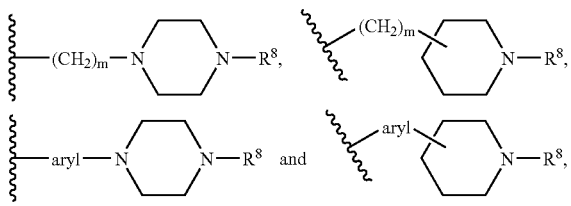

wherein one or more of the aryl and/or one or more of the heteroaryl in the above-noted definitions for $R^2$ can be unsubstituted or optionally substituted with one or more moieties which can be the same or different, each moiety being independently selected from the group consisting of halogen, —CN, —$OR^5$, —$SR^5$, —$S(O_2)R^6$, —$S(O_2)NR^5R^6$, —$NR^5R^6$, —$C(O)NR^5R^6$, $CF_3$, alkyl, aryl and $OCF_3$ and $R^5$ $R^6 R^8$, and $R^9$ are defined above in the definitions for formula V.

The process of making the compound of formula I comprises:

(a) reacting a compound of formula II

(II)

with a compound of formula III

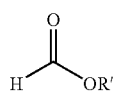

(III)

where R' is alkyl, substituted alkyl, alkenyl, substituted alkenyl, alkynyl, substituted alkynyl, aryl, substituted aryl, heteroaryl, substituted heteroaryl, aralkyl, substituted aralkyl, alkylaryl, substituted alkylaryl, cycloalkyl, substituted cycloalkyl, heterocycyl or optionally substituted heterocycyl, in the presence of lithium diisopropyl amide ("LDA"), lithium bis(trimethylsilyl)amide ("LiHMDS"), potassium bis(trimethylsilyl)amide ("KHMDS") or sodium bis(trimethylsilyl)amide ("NaHMDS"), and a solvent at a temperature between about —100° C. to about 0° C. to give a compound of formula IV

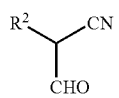

(IV)

and b) reacting a compound of formula IV with hydrazine and acetic acid in an alcoholic solvent at a temperature between about 50° C. to about 150° C. to give a compound of formula I.

DETAILED DESCRIPTION OF THE INVENTION

The inventive process which makes the compounds of formula I has several advantages: it is economical, comprises two steps and produces the compounds of formula I in a higher yield that the other prior processes.

As used above, and throughout this disclosure, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl and 3-methylbut-2-enyl. The term "substituted alkenyl" means that the alkenyl group may be substituted by one or more substituents which may be the same or different, each substituent being independently selected from the group consisting of alkyl, aryl and cycloalkyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

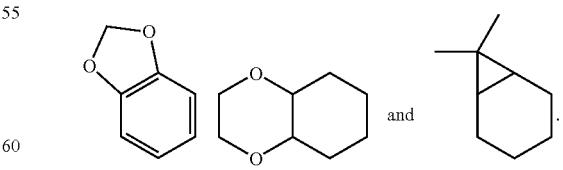

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S, S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

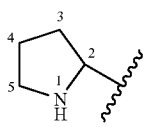

there is no —OH attached directly to carbons marked 2 and 5.

It should also be noted that tautomeric forms such as, for example, the moieties:

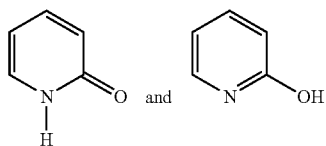

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences is assumed to have the hydrogen atom(s) to satisfy the valences.

When any variable (e.g., aryl, heterocycle, $R^2$, etc.) occurs more than one time in any constituent or in Formula V, its definition on each occurrence is independent of its definition at every other occurrence.

In one embodiment, the invention discloses a novel, easy to use process for preparing compounds of formula I comprising two steps.

In the first step the starting nitrile of formula II is added to a suitable solvent under anhydrous conditions. After cooling the solution to a temperature range of about −100° C. to about 0° C., LDA, LiHMDS, KHMDS, or NaHMDS is added to the solvent and the reaction mixture is stirred. Preferred temperature ranges are, for example, from about −80° C. to about −30° C. and from about −80° C. to about −70° C. being especially preferred. LiHMDS is an especially preferred base. Tetrahydrofuran (THF) is a preferred solvent when the base is LDA. A preferred solvent when the base is LiHMDS, KHMDS, or NaHMDS is diethyl ether or THF. Preferred reaction times range from about 1 to 4 hours, with 1 to 2 hours being especially preferred, with the determination of the exact time being well within the routine still of the practitioner.

After stirring is complete a compound of formula II is added to the reaction mixture and stirred, preferably while maintaining the reaction temperature. Again, determining the reaction time is well within the skill level of the practitioner, but is generally from about 30 minute to 2 hours, with 0.5 to 1 hour being especially preferred. The reaction is then quenched with an agent such as saturated ammonia chloride, again preferably while maintaining the reaction temperature and the compound of formula IV with or without isolation is collected by conventional means. In terms of amounts, generally from about 0.05 mole to about 3 moles of a compound of formula II and from about 0.025 mole to about 1.5 moles of a compound of formula III are used. The amount of base used is from about 0.5 mole to about 3 moles.

In the next step a reaction mixture comprising the compound of formula IV and an alcoholic solvent is formed. Hydrazine, with hydrazine monohydrate being especially preferred, is added to the reaction mixture followed by the addition of acetic acid and the reaction mixture is heated at a temperature form about 50° C. to about 150° C., with from about 70° C. to about 100° C. being especially preferred, for a period of time generally ranging from about 2 hr to about 60 hours, with about 20 to about 40 being especially preferred. Again the determination of the exact time is well with the skill of the practitioner. Generally, the amount of hydrazine ranges from 0.05 to 3 mol, and the amount of acetic acid ranges from about 0.001 to 2 mol, with 0.008 to 0.5 mol being especially preferred. The solvent is then removed under reduced pressure and the crude product is purified by either washing with brine or distillation.

Preferred compounds for formula I prepared by the inventive process include those wherein $R^2$ is halogen, $CF_3$, CN, lower alkyl, alkyl substituted with —$OR^6$, alkynyl, aryl, heteroaryl or heterocyclyl.

In an additional embodiment, compound of formula I wherein $R^2$ is halogen, $CF_3$, CN, lower alkyl, alkynyl, or alkyl substituted with —$OR^6$ are more preferred with and an additional embodiment wherein $R^2$ is lower alkyl, alkynyl or Br or especially ethyl, being most preferred.

The invention disclosed herein is exemplified by the following preparations and examples which should not be construed to limit the scope of the disclosure.

EXAMPLES

The following solvents and reagents may be referred to by their abbreviations in parenthesis:
tertiary butoxycarbonyl: Tboc
tetrahydrofuran: THF
lithium bis(trimethylsilyl)amide: LiHMDS
ethanol: EtOH
acetic acid: HOAc
potassium t-butoxide: t-BuOK
dichloromethane: DCM
liter: L
milliliters: mL
grams: g
room temperature or rt (ambient): about 25° C.
mole: mol.

Example 1

Preparation of Preparation of
3-amino-4-ethyl-pyrazole

Butyronitrile (207.6 g, 3 mol) and anhydrous THF (8 L) were introduced into a three-necked round bottom flask equipped with a mechanical stirrer, a thermometer and a 2 L pressure-equalizing funnel, which had been kept under dry nitrogen. The solution was cooled to −72° C. (acetone-dry ice) and a solution of LiHMDS 1.0M in THF (3 L, 3 mol, 2 eq.) was added dropwise over a 45 minute period and the reaction mixture was stirred for 1 hr. Next a solution of ethylformate 111 g (1.5 mol, 1 eq.) dissolved in 200 ml of THF was added via a 500 mL addition funnel over a 30 min period. Upon completion of the reaction, the reaction mixture was stirred for 30 min at −72° C.

The reaction was quenched with saturated ammonia chloride solution (3 L) at −72° C. and stirred for 10 min. The reaction mixture was filtered and the collected solid was washed with diethyl ether (4×1 L) before being discarded. The filtrate was dried over magnesium sulfate and filtered again. The filtrate was concentrated under reduced pressure with a warm water bath (<30° C.) to leave a 450 g of a yellow solution.

The yellow solution was diluted with ethanol (200 proof, 2 L) and charged into a reaction vessel, equipped with a magnetic stirring bar and heating oil bath. Hydrazine monohydrate (180 mL, 2 eq.) was added to the reaction vessel while stirring followed by the addition of HOAC (64 ml., 0.35 eq.). The reaction vessel was then sealed and the mixture was heated to 80° C. for 40 hours.

The reaction mixture was concentrated under reduced pressure in a hot water bath (50° C.) to remove completely all the solvent and yielded 219 g of a crude oil. The crude oil was diluted with methylene chloride (2 L) and washed with brine (400 mL). The phases were partitioned and the pH values was monitored (pH ~9). The organic phases were combined and extracted with methylene chloride (2×1 L). The filtrate was concentrated under reduced pressure to dryness to 106 g of light yellow oil (3-amino-4-ethylpyrazole), which was solidified under vacuum. Yield 65%.

Comparative Example 1

Preparation of 3-amino-4-ethyl-pyrazole (Not According to the Invention)

Butyronitrile (190 g, 2.25 mol) and ethylformate (305 g, 4.12 mol) were added to a reaction vessel containing a suspension of t-BuOK (308 g, 2.25 mol) in diethyl ether (7 L), which was at a temperature between −10° C. to 0° C., over a 4 hr period during which the reaction temperature was maintained between −5° C. to 12° C. The reaction mixture was then stirred overnight at room temperature.

The reaction mixture was then cooled to −10° C. and HOAC (160 ml) was slowly added while maintaining the reaction temperature between −5° C. to 0° C. followed with stirring the reaction mixture for 10 min. The reaction mixture was then filtered and the solid was washed with diethyl ether (2×500 ml). The filtrate was then concentrated at 50° C. to yield 250 g of a light yellow oil.

The oil was dissolved into dry EtOH (350 mL) and hydrazine hydrate (132 ml) was added while maintaining a reaction temperature of 20° C. to 30° C., followed by the addition of HOAc at 30° C. to 40° C. The reaction mixture was then refluxed at 72° C. overnight.

The solvent was removed at 65° C. to 70° C. to yield 165 g of yellow oil. The oil was dissolved in 1 L of DCM and brine (250 mL). The layers were separated and the DCM layer was washed with brine (150 mL). The aqueous layers were combined and washed with DCM (2×500 ml.) and the combined DCM layers were washed again with brine (150 ml). The DCM layers were combined, and dried with sodium sulfate/magnesium sulfate. The solvent was removed to yield an oil which solidified at room temperature to give 70 g 3-amino-4-ethyl-pyrazole. Yield 23%.

The above description of the invention is intended to be illustrative and not limiting. Various changes or modifications in the embodiments described herein may occur to those skilled in the art. These changes can be made without departing from the scope or spirit of the invention

What is claimed is:

1. A process of making a 3-amino-4-substituted pyrazole derivative of the formula:

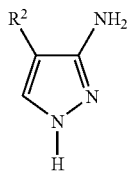

(I)

in which $R^2$ is selected from the group consisting of $R^9$, alkyl, alkenyl, alkynyl, $CF_3$, heterocyclyl, heterocyclylalkyl, halogen, haloalkyl, aryl, arylalkyl, heteroarylalkyl, alkynylalkyl, cycloalkyl, heteroaryl, alkyl substituted with 1-6 $R^9$ groups which can be the same or different and are independently selected from the list of $R^9$ shown below, aryl substituted with 1-3 aryl or heteroaryl groups which can be the same or different and are independently selected from phenyl, pyridyl, thiophenyl, furanyl and thiazolo groups, aryl fused with an aryl or heteroaryl group, heteroaryl substituted with 1-3 aryl or heteroaryl groups which can be the same or different and are independently selected from phenyl, pyridyl, thiophenyl, furanyl and thiazolo groups, heteroaryl fused with an aryl or heteroaryl group,

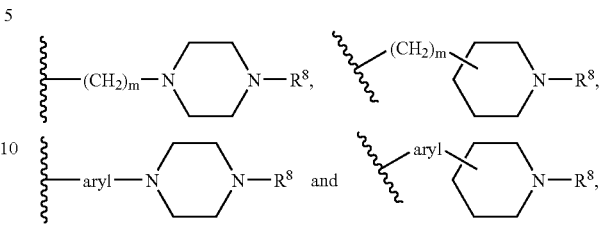

wherein one or more of the aryl and/or one or more of the heteroaryl in the above-noted definitions for $R^2$ can be unsubstituted or optionally substituted with one or more moieties which can be the same or different, each moiety being independently selected from the group consisting of halogen, —CN, —$OR^5$, —$SR^5$, —$S(O_2)R^6$, —$S(O_2)NR^5R^6$, —$NR^5R^6$, —$C(O)NR^5R^6$, $CF_3$, alkyl, aryl and $OCF_3$;

$R^4$ is H, halo or alkyl;

$R^5$ is H, alkyl, aryl or cycloalkyl;

$R^6$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, —$OR^5$, —$NR^5R^{10}$, —$C(R^4R^5)_p$—$R^9$, —$N(R^5)Boc$, —$(CR^4R^5)_pOR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^7$ is selected from the group consisting of alkyl, cycloalkyl, aryl, arylalkenyl, heteroaryl, arylalkyl, heteroarylalkyl, heteroarylalkenyl, and heterocyclyl, wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

$R^8$ is selected from the group consisting of $R^6$, —$OR^6$, —$C(O)NR^5R^{10}$, —$S(O_2)NR^5R^{10}$, —$C(O)R^7$, —$C(=N-CN)-NH_2$, —$C(=NH)-NHR^5$, heterocyclyl, and —$S(O_2)R^7$;

$R^9$ is selected from the group consisting of halogen, —CN, —$NR^5R^{10}$, —$C(O_2)R^6$, —$C(O)NR^5R^{10}$, —$OR^6$, —$SR^6$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, —$OR^5$, —$NR^4R^5$, —$C(R^4R^5)_p$—$R^9$, —$N(R^5)Boc$, —$(CR^4R^5)_pOR^5$, —$C(O_2)R^5$, —$C(O)NR^4R^5$, —$C(O)R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$; or optionally (i) $R^5$ and $R^{10}$ in the moiety —$NR^5R^{10}$, or (ii) $R^5$ and $R^6$ in the moiety —$NR^5R^6$, may be joined together to form a cycloalkyl or heterocyclyl moiety, with each of said cycloalkyl or heterocyclyl moiety being unsubstituted or optionally independently being substituted with one or more $R^9$ groups; and m is 0 to 4 which comprises:

(a) reacting a compound of formula II

(II)

with a compound of formula III

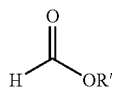
(III)

where R' is alkyl, substituted alkyl, alkenyl, substituted alkenyl, alkynyl, substituted alkynyl, aryl, substituted aryl, heteroaryl, substituted heteroaryl, aralkyl, substituted aralkyl, alkylaryl, substituted alkylaryl, cycloalkyl, substituted cycloalkyl, heterocycyl or substituted heterocycyl, in the presence of LDA, LiHMDS, KHMDS, or NaHMDS and a solvent at a temperature between about −100° C. to about 0° C. to give a compound of formula IV

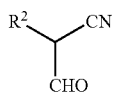
(IV)

and b) reacting a compound of formula IV with hydrazine and acetic acid in an alcoholic solvent at a temperature between about 50° C. to about 150° C. to give a compound of formula I.

2. The process according to claim 1 wherein the base is LDA and the solvent is THF.

3. The process according to claim 2, wherein $R^2$ is a lower alkyl group, or a cycloalkyl group and R' is a lower alkyl group that is optionally substituted by phenyl.

4. The process according to claim 2, wherein $R^2$ is halogen, $CF_3$, CN, lower alkyl, alkyl substituted with —$OR^6$, alkynyl, aryl, heteroaryl or heterocyclyl.

5. The process according to claim 2, wherein $R^2$ is Br, Cl, cyclopropyl or ethynyl.

6. The process according to claim 2, wherein the alcoholic solvent is methanol, ethanol, propanol, isopropanol or butanol.

7. The process according to claim 6 wherein the alcoholic solvent is ethanol.

8. The process according to claim 7, wherein $R^2$ is ethyl.

9. The process according to claim 2, wherein the reaction temperature in step a) is about −80° C. to about −30° C.

10. The process according to claim 2, wherein the reaction temperature in step a) is about −80° C. to about −70° C.

11. The process according to claim 8, wherein the reaction temperature in step a) is about −80° C. to about −70° C.

12. The process according to claim 10, wherein the reaction temperature in step b) is about 70° C. to about 100° C.

13. The process according to claim 1 wherein the base is LiHMDS and the solvent is THF.

14. The process according to claim 13, wherein $R^2$ is a lower alkyl group or a cycloalkyl group and R' is a lower alkyl group that is optionally substituted by phenyl.

15. The process according to claim 13, wherein $R^2$ is halogen, $CF_3$, CN, lower alkyl, alkyl substituted with —$OR^6$, alkynyl, aryl, heteroaryl or heterocyclyl.

16. The process according to claim 13, wherein $R^2$ is Br, Cl, cyclopropyl or ethynyl.

17. The process according to claim 13, wherein the alcoholic solvent is methanol, ethanol, propanol, isopropanol or butanol.

18. The process according to claim 17 wherein the alcoholic solvent is ethanol.

19. The process according to claim 18, wherein $R^2$ is ethyl and the base is LiHMDS.

20. The process according to claim 13, wherein the reaction temperature in step a) is about −80° C. to about −30° C.

21. The process according to claim 13, wherein the reaction temperature in step a) is about −80° C. to about −70° C.

22. The process according to claim 19, wherein the reaction temperature in step a) is about −80° C. to about −70° C.

23. The process according to claim 20, wherein the reaction temperature in step b) is about 70° C. to about 100° C.

24. The process according to claim 1, wherein the base is LiHMDS and the solvent is diethyl ether.

25. The process according to claim 1, wherein the base is KHMDS or NaHMDS.

* * * * *